United States Patent
Jang et al.

(10) Patent No.: US 10,089,736 B2
(45) Date of Patent: Oct. 2, 2018

(54) LOCAL HIGH-RESOLUTION IMAGING METHOD FOR THREE-DIMENSIONAL SKELETAL IMAGE AND APPARATUS THEREFOR

(71) Applicant: Korea Advanced Institute of Science and Technology, Daejeon (KR)

(72) Inventors: InGwun Jang, Daejeon (KR); Jung Jin Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/331,620

(22) Filed: Oct. 21, 2016

(65) Prior Publication Data
US 2018/0018766 A1 Jan. 18, 2018

(30) Foreign Application Priority Data

Jul. 14, 2016 (KR) .................. 10-2016-0089456

(51) Int. Cl.
*G06K 9/00* (2006.01)
*G06K 9/46* (2006.01)
(Continued)

(52) U.S. Cl.
CPC ............ *G06T 7/0012* (2013.01); *A61B 5/055* (2013.01); *A61B 5/4509* (2013.01); *A61B 6/032* (2013.01); *A61B 6/505* (2013.01); *A61B 6/5205* (2013.01); *G06K 9/4604* (2013.01); *G06K 9/4671* (2013.01); *G06T 11/008* (2013.01); *G06T 17/205* (2013.01); *H04N 5/23245* (2013.01); *A61B 2576/02* (2013.01); *G06T 2207/30008* (2013.01)

(58) Field of Classification Search
CPC ....... A61B 5/4509; A61B 6/032; A61B 6/505; A61B 6/5205; G06T 17/205

USPC ........ 382/128, 173, 190, 258, 131; 600/427, 600/407, 410, 411, 425, 437, 439; 703/2; 706/45; 378/54; 345/419
See application file for complete search history.

(56) References Cited

U.S. PATENT DOCUMENTS

| | | | |
|---|---|---|---|
| 2005/0031179 A1* | 2/2005 | Wehrli | G01N 24/08 382/131 |
| 2005/0207630 A1* | 9/2005 | Chan | A61B 6/466 382/131 |
| 2008/0259074 A1* | 10/2008 | Tian | A61B 5/0073 345/419 |

FOREIGN PATENT DOCUMENTS

| KR | 101531654 B1 | 6/2015 |
|---|---|---|
| KR | 10-2016-0068647 A | 6/2016 |

OTHER PUBLICATIONS

Bong-Ju Kim et al., "A Biomechanical Study on a New Surgical Procedure for the Treatment of Intertrochanteric Fractures in relation to Osteoporosis of Varying Degrees", Oct. 9, 2003, pp. 401-pp. 410.

* cited by examiner

*Primary Examiner* — Charlotte M Baker
(74) *Attorney, Agent, or Firm* — Masuvalley & Partners

(57) ABSTRACT

A local high-resolution imaging method and apparatus for a three-dimensional (3D) skeletal image is provided. The method includes determining a volume of interest (VOI) to perform high-resolution imaging from the 3D skeletal image in which an object to be inspected is captured, localizing the VOI based on a finite element method (FEM), and setting a multi-resolution constraint based on a bone mineral density (BMD) between the 3D skeletal image and the localized VOI and reconstructing a skeletal image in which high-resolution imaging is performed on the localized VOI.

13 Claims, 10 Drawing Sheets

(51) Int. Cl.
*G06T 7/00* (2017.01)
*A61B 5/055* (2006.01)
*A61B 5/00* (2006.01)
*A61B 6/03* (2006.01)
*A61B 6/00* (2006.01)
*G06T 11/00* (2006.01)
*G06T 17/20* (2006.01)
*H04N 5/232* (2006.01)

LOCAL HIGH-RESOLUTION IMAGING METHOD FOR THREE-DIMENSIONAL SKELETAL IMAGE AND APPARATUS THEREFOR

CROSS-REFERENCE TO RELATED APPLICATIONS

A claim for priority under 35 U.S.C. § 119 is made to Korean Patent Application No. 10-2016-0089456 filed Jul. 14, 2016, in the Korean Intellectual Property Office, the entire contents of which are hereby incorporated by reference.

BACKGROUND

Embodiments of the inventive concepts described herein relate to high-resolution imaging technologies of improving resolution of a three-dimensional (3D) medical image based on bone remodeling simulations and reconstructing a skeletal image as a high-resolution image.

A prevalence rate of osteoporosis of domestic people who are older 50 is very high to have 34.9% of females and 7.8% of males. Globally, about 200 million women suffer from osteoporosis now. For example, 10% of women over 60, 20% of those over 70, 40% of those over 80, and 75% of those over 90 are affected for each age. In addition, the prevalence rate of osteoporosis is steadily increasing as society ages.

Osteoporosis represents a state of a high possibility that fractures will occur since bone strength is weak due to reduced bone mass and a qualitative change. Herein, the bone strength may refer to a force in which a bone resists its fracture. This is determined by 'bone mass' and 'bone quality'.

Osteoporosis finally causes osteoporotic fractures by reducing bone mass and weakening bone quality. The osteoporotic fractures cause enormous economic damage as well as degrade the quality of personal life by accompanying complications together with a serious mobility impairment. For example, according to research by the Unites States, medical costs by osteoporotic fractures are $18 billion every year. It is very important to perform an early diagnosis through skeletal medical images since this osteoporosis has no special subjective symptoms. However, after 30% to 50% of most bone mass is lost, people realize that they suffer from osteoporosis due to the occurrence of fractures by external impacts. As such, late realization for osteoporosis results in a high fatality rate and serious sequelae. A trabecular bone network cut once may not be restored to a previously connection state by medical treatment due to irreversibility of 'bone remodeling' using current medical technologies. In addition, assuming that there is the same bone mass loss, since a decrease in connectivity of trabeculae has more influence on bone strength than a decrease in thickness of the trabeculae, it is very important to maintain connectivity of bone microstructures. In other words, it is clinically important to perform an early diagnosis of osteoporosis.

In general, the diagnosis of osteoporosis is indirectly made by measuring bone mineral density (BMD). Dual energy X-ray absorptiometry (DXA), quantitative computed tomography (QCT), and the like are used as representative BMD measurement methods. The DXA is to measure average BMD for a volume of interest (VOI) of a lumbar spine and a femur, to obtain a T-score for average BMD of a healthy adult, and to perform diagnosis of 'normal (T≥−1.0)', 'osteopenia (−1.0≤T≤−2.5)', and 'osteoporosis (T≤−2.5)' based on the BMD T-score. The DXA is the most widely used in the world today due to a short measurement time, a low amount of radiation, a low measurement cost, and the like. However, the DXA obtains only 'bone mass' information based on an X-ray attenuation difference, but does not provide information about 'bone quality' such as a bone microstructure of a trabecular bone. Due to absence of information about a bone microstructure, if two objects having different bone microstructures (herein, it is assumed that genders, ages, and the like are the same as each other) have the same average BMD value, there is a situation of giving the same diagnosis of osteoporosis irrespective of different bone strength. In other words, a possibility of misdiagnosis is always present. A fracture risk assessment tool (FRAX) is provided as a method for solving the problem of the DXA and is attempted to perform clinical application.

Since bone strength is determined by a structure of a trabecular bone as well as BMD, a method of simply measuring only BMD may predict only 64% of mechanical bone strength, but may predict 94% of the mechanical bone strength in case of considering a 3D structure. In other words, it is essential to perform a quantitative structure analysis for a trabecular bone for the reliable early diagnosis of the osteoporosis. If BMD measurement is combined with a bond structure analysis, it is possible to perform a more accurate diagnosis of osteoporosis. Quantitative estimation for bone strength is recently attempted by linking high resolution peripheral QCT (HR-pQCT) which may capture bone microstructures to a finite element analysis. In the HR-pQCT, there is a limitation that it is impossible to capture a significant lumbar spine and femur in the diagnosis of osteoporosis.

A medical imaging device plays an important role in the diagnosis and treatment of disease by imaging information about a human body in a quantitative manner. Computer tomography (CT) and magnetic resonance imaging (MRI) are the best examples of the medical imaging device. In case of CT and MRI, a signal detector decreases in size to obtain a high-resolution image to increase the number per unit area. However, since a current maximum resolution is an in-plane resolution of 0.2×0.2 mm$^2$, it is impossible to capture a bone microstructure. In addition, it is possible for recently developed HR-pQCT to obtain a high-resolution image (an image with a level of 50 μm) and to have a limitation in a capturing portion such as a wrist and an ankle. As described above, it is impossible to capture a femur or a lumbar spine which is a diagnosis portion of osteoporosis.

There is a method of solving a hardware-like limitation of this medical imaging device by softwarily accessing the medical imaging device. For example, image processing such as compressed sensing for an image captured by the medical imaging device is performed, and an original image is reconstructed based on some extracted data. In addition, there is a super resolution processing method performed in image post-processing. However, in case of an image processing method such as compressed sensing and super resolution, it is possible to perform any high-resolution imaging of medical images, but there is a limitation that the image processing method does not provide a high-resolution image of a degree to analyze a 3D microstructure.

Thus, there is a need for high-resolution imaging technologies of performing local high-resolution imaging for a low-resolution image based on bone remodeling simulations to verify a bone microstructure. Korean Patent No.

10-1531654 discloses technologies of reconstructing a 3D image by improving a convergence speed using compressed sensing.

SUMMARY

Embodiments of the inventive concepts provide an apparatus and method for reconstructing a skeletal image to ascertain a microstructure by performing local high-resolution imaging for a low-resolution skeletal image based on bone remodeling simulations.

Embodiments of the inventive concepts provide an apparatus and method for reducing an amount of calculation according to the performance of a finite element method (FEM) for a 3D skeletal image by setting a phenomenological local load condition for a volume of interest (VOI) corresponding to part of a skeletal image rather than the entire skeletal image and localizing the VOI.

Embodiments of the inventive concepts provide an apparatus and method for improving convergence by setting a multi-resolution constraint and performing topology optimization.

Embodiments of the inventive concepts provide an apparatus and method for reducing misdiagnosis according to diagnosing osteoporosis based on only bone mineral density (BMD) and more accurately performing an early diagnosis of a lesion such as osteoporosis by linking and providing bone stiffness which may be calculated through a high-resolution image and the FEM with osteoporosis diagnosis criteria, that is, providing an image in which high-resolution imaging is performed to represent BMD and a microstructure.

Embodiments of the inventive concepts provide an apparatus and method for reducing an amount of radiation exposure exposed to a human body when an image is captured to diagnose osteoporosis and the like by performing local high-resolution imaging for a VOI in image post-processing rather than image reconstruction, and providing convenience of an object to be inspected (e.g., a patient) and may increase profitability of a hospital by securing a short capturing time.

One aspect of embodiments of the inventive concept is directed to provide a local high-resolution imaging method for a 3D skeletal image. The method may include determining a volume of interest (VOI) to perform high-resolution imaging on the 3D skeletal image in which an object to be inspected is captured, localizing the VOI based on a finite element method (FEM), and setting a multi-resolution constraint based on a bone mineral density (BMD) between the 3D skeletal image and the localized VOI and reconstructing a skeletal image in which high-resolution imaging is performed on the localized VOI.

The localizing of the VOI may include performing the FEM for the skeletal image in which the object to be inspected is captured, extracting a displacement corresponding to a cut boundary of the VOI based on a previously defined load condition, performing the FEM for the VOI by applying the extracted displacement to a boundary condition, and extracting a reaction force corresponding to a cut boundary of the VOI in which the FEM is performed and setting the extracted reaction force as a local load condition.

The reconstructing of the skeletal image in which the high-resolution imaging is performed may include setting a separate voxel value in a high-resolution image as a design variable, setting compliance of the VOI as an objective function indicating a strain energy of the VOI, and setting a BMD difference between the high-resolution image and a low-resolution image as the multi-resolution constraint.

The high-resolution image may be generated by subdividing a voxel of a low-resolution image corresponding to the VOI included in the 3D skeletal image.

The reconstructing of the skeletal image in which the high-resolution is performed may include reconstructing a bone microstructure for the VOI by performing topology optimization for a finite element model corresponding to the high-resolution image.

The determining of the VOI may include determining a plurality of VOIs on the skeletal image and verifying a trabecular bone corresponding to each of the VOIs based on a skeletal image, in which high-resolution imaging is performed, reconstructed for the plurality of VOIs.

Another aspect of embodiments of the inventive concept is directed to provide a local high-resolution imaging apparatus for a 3D skeletal image. The apparatus may include a VOI determining unit configured to determine a VOI to perform high-resolution imaging on the 3D skeletal image in which an object to be inspected is captured, a VOI localizing unit configured to localize the VOI based on an FEM, and an image reconstructing unit configured to set a multi-resolution constraint based on a BMD between the 3D skeletal image and the localized VOI and to reconstruct a skeletal image in which high-resolution imaging is performed on the localized VOI.

The VOI localizing unit may perform the FEM for the skeletal image in which the object to be inspected is captured, may extract a displacement corresponding to a cut boundary of the VOI based on a previously defined load condition, may perform the FEM for the VOI by applying the extracted displacement to a boundary condition, and may extract a reaction force corresponding to a cut boundary of the VOI in which the FEM is performed and may set the extracted reaction force as a local load condition.

The image reconstructing unit may set a separate voxel value in a high-resolution image as a design variable, may set compliance of the VOI as an objective function indicating a strain energy of the VOI, and may set a BMD difference between the high-resolution image and a low-resolution image as the multi-resolution constraint.

The high-resolution image may be generated by subdividing a voxel of a low-resolution image corresponding to the VOI included in the 3D skeletal image.

The image reconstructing unit may reconstruct a bone microstructure for the VOI by performing topology optimization for a finite element model corresponding to the high-resolution image.

The VOI determining unit may determine a plurality of VOIs on the skeletal image and may verify a trabecular bone corresponding to each of the VOIs based on a skeletal image, in which high-resolution imaging is performed, reconstructed for the plurality of VOIs.

Still aspect of embodiments of the inventive concept is directed to provide a local high-resolution imaging apparatus for a 3D skeletal image. The apparatus may include a memory into which at least one program is loaded and at least one processor. The at least one processor may determine a VOI to perform high-resolution imaging on the 3D skeletal image in which an object to be inspected is captured, may localize the VOI based on an FEM, and may set a multi-resolution constraint based on a BMD between the 3D skeletal image and the localized VOI and may reconstruct a skeletal image in which high-resolution imaging is performed on the localized VOI, under control of the at least one program.

The localizing of the VOI may include performing the FEM for the skeletal image in which the object to be inspected is captured, extracting a displacement corresponding to a cut boundary of the VOI based on a previously defined load condition, performing the FEM for the VOI by applying the extracted displacement to a boundary condition, and extracting a reaction force corresponding to a cut boundary of the VOI in which the FEM is performed and setting the extracted reaction force as a local load condition.

The reconstructing of the skeletal image in which the high-resolution imaging is performed may include setting a separate voxel value in a high-resolution image as a design variable, setting compliance of the VOI as an objective function indicating a strain energy of the VOI, and setting a BMD difference between the high-resolution image and a low-resolution image as the multi-resolution constraint.

Still aspect of embodiments of the inventive concept is directed to provide a computer-readable storage medium including instructions for controlling a computer system to perform high-resolution imaging of a 3D skeletal image. The instructions may control the computer system by a method including determining a VOI to perform the high-resolution imaging on the 3D skeletal image in which an object to be inspected is captured, localizing the VOI based on an FEM, and setting a multi-resolution constraint based on a BMD between the 3D skeletal image and the localized VOI and reconstructing a skeletal image in which high-resolution imaging is performed on the localized VOI.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
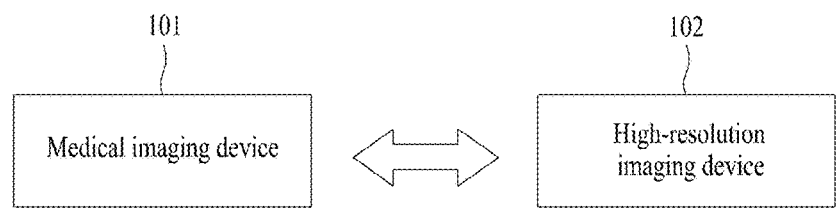
FIG. 1 is a block diagram schematically illustrating a medical imaging device and a high-resolution imaging device in an embodiment of the inventive concept.

Hereinafter, a description will be given in detail for exemplary embodiments of the inventive concept with reference to the accompanying drawings. However, the inventive concept is not limited by exemplary embodiments. Also, with respect to the descriptions of the drawings, like reference numerals refer to like elements.

Embodiments relate to technologies of performing high-resolution imaging for a skeletal image based on bone remodeling. In detail, embodiments localize a volume of interest (VOI) among regions into which a 3D skeletal image is segmented and perform high-resolution imaging of the localized VOI, and relate to technologies of reconstructing the localized VOI as an image in which high-resolution imaging is performed in image post-processing to read out a bone microstructure as well as bone mineral density (BMD). Particularly, embodiments relate to technologies of localizing a VOI by providing a method for estimating or setting a phenomenological local load condition for the VOI such that an enormous amount of calculation requested upon a finite element method (FEM) is reduced to reconstruct a skeletal image as an image in which high-resolution imaging is performed. Embodiments relate to a method for providing a method for setting a multi-resolution constraint applied upon reconstructing an image which represents a bone microstructure through topology optimization (i.e., bone remodeling simulations) for a localized VOI. In other words, embodiments relate to technologies of performing local high-resolution imaging for a low-resolution skeletal image through the topology optimization (i.e., the bone remodeling simulations).

In embodiments, the term "topology optimization" may represent a method for reconstructing a structure having maximum stiffness by redistributing the density of an element with respect to a load element using minimum mass. Embodiments may reconstruct a bone microstructure which obtains maximum mechanical efficiency by reallocating a trabecular bone with respect to a mechanical stimulus using minimum bone mass through topology optimization. The term "mechanical stimulus" may represent a force provided to a femur and the like upon standing or running, and the like.

In embodiments, the term "bone microstructure" may mean the product of bone remodeling which repeatedly performs bone resorption and bone formation by an external mechanical stimulus. In other words, a bone microstructure may be reconstructed by copying a bone remodeling process. The term "bone remodeling" may represent a process of reallocating a trabecular to obtain maximum mechanical efficiency using minimum mass. Bone remodeling simulations through topology optimization may indicate a process of searching for a structure having maximum stiffness under a given mass condition.

In embodiments, the term "voxel" may represent a value on a regular grid in a 3D space and may represent graphic information of a one end which defines one point of the 3D space. For example, each coordinate in three dimensions may represent a location, a color, and density.

FIG. 1 is a block diagram schematically illustrating a medical imaging device and a high-resolution imaging device in an embodiment of the inventive concept.

Referring to FIG. 1, a medical imaging device 101 may be a device which captures an object to be inspected to diagnose osteoporosis, measure bone mineral density (BMD), and check a bone microstructure.

Herein, the medical imaging device 101 may include all medical devices, each of which converts the intensity of an image in which the object to be inspected is captured into a modulus of elasticity. For example, the medical imaging device 101 may include all medical imaging devices, such as a computer tomography (CT) device, a quantitative computed tomography (QCT) device, and a magnetic resonance imaging (MRI) device, which may convert the intensity of an image into the a modulus of elasticity. The object to be inspected may be a specific body portion captured to measure BMD, for example, a thigh, a hip joint, a wrist, an ankle, a knee, a lumbar vertebra, and the like.

As such, the medical imaging device 101 may capture the object to be inspected and may send the captured information to a high-resolution imaging device 102. For example, if the QCT device captures the object to be inspected, it may detect X rays which penetrate the object to be inspected and may send the detected X rays to the high-resolution imaging device 102. The high-resolution imaging device 102 may generate a low-resolution QCT image based on the received X rays.

The high-resolution imaging device 102 may perform high-resolution imaging for a low-resolution medical image to reconstruct the low-resolution medical image as a high-resolution image by performing a finite element method (FEM) and topology optimization based on the medical image. For example, the high-resolution imaging device 102 may perform local high-resolution imaging for a VOI which is a portion into which a low-resolution 3D skeletal image is segmented. For this local high-resolution imaging, the high-resolution imaging device 102 may select a phenomenological local load condition, may localize the VOI, and may apply a multi-resolution constraint to read out a bone microstructure.

The high-resolution imaging device 102 may connect with the medical imaging device 101 by wire or wirelessly and may be combined with the medical imaging device 100 by an add-one type. For example, a computer system, a workstation, and the like may be used as the high-resolution imaging device 102.

Hereinafter, a description will be given below for an operation of performing high-resolution imaging for a skeletal image based on the FEM and the topology optimization with reference to FIGS. 2 and 3.

Figure 2:
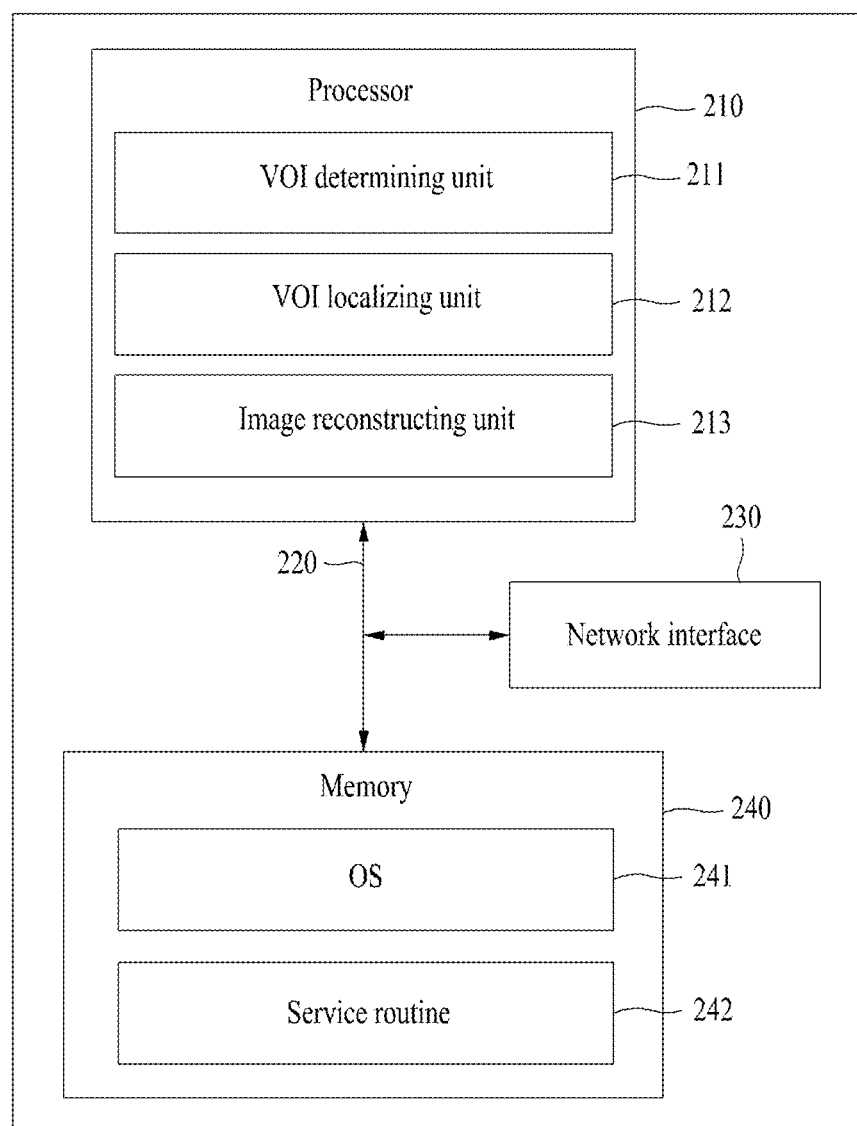
FIG. 2 is a block diagram illustrating a detailed configuration of a high-resolution imaging device in an embodiment of the inventive concept.

FIG. 2 is a block diagram illustrating a detailed configuration of a high-resolution imaging device in an embodiment of the inventive concept. FIG. 3 is a flowchart illustrating a local high-resolution imaging method in an embodiment of the inventive concept.

A high-resolution imaging device 200 according to an embodiment may include a processor 210, a bus 220, a network interface 230, and a memory 240. The memory 240 may include an operating system (OS) 241 and a service routine 242. The processor 210 may include a VOI determining unit 211, a VOI localizing unit 212, and an image reconstructing unit 213. In other embodiments, the high-resolution imaging device 200 may include more components than those of FIG. 2. However, there is no need for clearly illustrating most conventional components. For example, the high-resolution imaging device 200 may include another component such as a display or a transceiver.

The memory 240 may be a computer-readable storage medium and may include a permanent mass storage device such as a random access memory (RAM), a read only memory (ROM), and a disc drive. Also, the memory 240 may store a program code for the OS 241 and the service routine 242. These software components may be loaded from a separate computer-readable storage medium independent of the memory 240 using a drive mechanism (not shown). This separate computer-readable storage medium may include a computer-readable storage medium (not shown) such as a floppy drive, a disc, a tape, a digital versatile disc/compact disc-ROM (DVD/CD-ROM) drive, and a memory card. In another embodiment, the software components may be loaded into the memory 240 via the network interface 230 rather than the computer-readable storage medium.

The bus 220 may perform communication and data transmission between the components of the high-resolution imaging device 200. The bus 220 may be configured using a high-speed serial bus, a parallel bus, a storage area network (SAN), and/or other suitable communication technologies.

The network interface 230 may a computer hardware component for connecting the high-resolution imaging device 200 with a computer network. The network interface 230 may connect the high-resolution imaging device 200 to the computer network over a wireless or wired connection.

The processor 210 may be configured to process a command of a computer program by performing basic calculation, a basic logic, and input and output calculation of the high-resolution imaging device 200. The command may be provided to the processor 210 via the bus 220 by the memory 240 or the network interface 230. The processor 210 may be configured to execute a program code for the VOI determining unit 211, the VOI localizing unit 212, and the image reconstructing unit 213. This program code may be stored in a storage device such as the memory 240.

Figure 3:
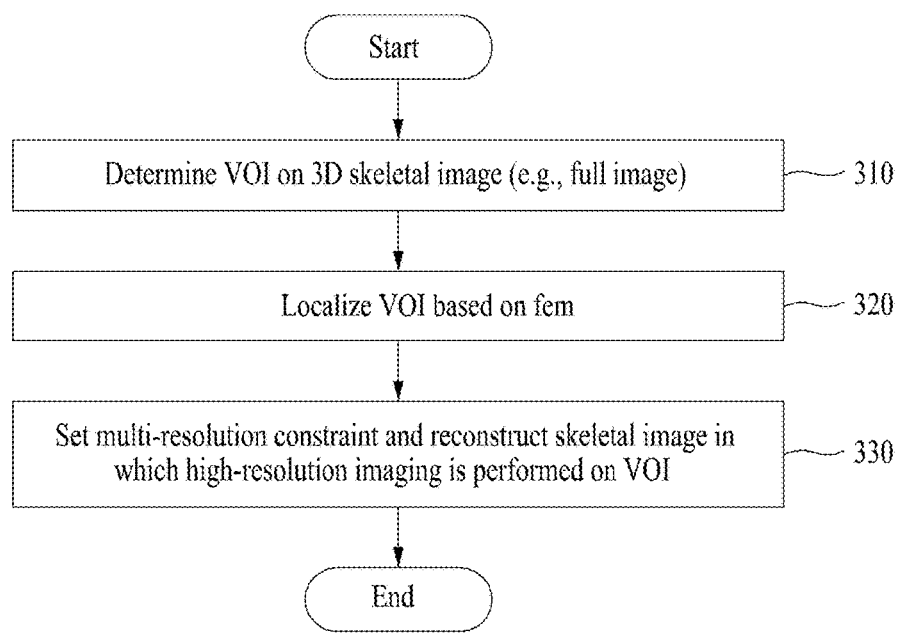
FIG. 3 is a flowchart illustrating a local high-resolution imaging method in an embodiment of the inventive concept.

The VOI determining unit 211, the VOI localizing unit 212, and the image reconstructing unit 213 may be configured to perform steps (e.g., steps 310 to 330) of FIG. 3.

In step 310, the VOI determining unit 211 may determine a VOI to perform high-resolution imaging, for a skeletal image (e.g., a full image) in which an object to be inspected is captured.

For example, the skeletal image may include skeletal images such as a spine image and a femur image among a plurality of images into which an image such as a QCT image, a CT image, or an MRI image is segmented through image segmentation. The VOI determining unit 211 may determine a partial specific portion to perform high-resolution imaging on a skeletal portion included in the skeletal image as the VOI. For example, a partial region such as a head, an upper portion, or a lower portion of a femur on the skeletal image may be determined as the VOI. Herein, the image in which the object to be inspected is captured may represent a 3D low-resolution image. For example, the image in which the object to be inspected is captured may represent a low-resolution image, resolution of which is higher than 300 µm.

In step 320, the VOI localizing unit 212 may localize the determined VOI based on a finite element method (FEM). For example, if there are three VOIs, a finite element model corresponding to each of the three VOIs may be generated. In other words, three finite element models may be generated.

A process of efficiently performing high-resolution imaging calculation, that is, reducing an amount of calculation, may be essential to apply the high-resolution imaging device 200 to actual clinical research. For example, if a proximal femur of an object to be inspected (e.g., a human body) is represented as a 3D finite element of 50 µm to 150 µm which is a thickness of a trabeculae, tens of millions of finite elements to hundreds of millions of finite elements may be required. As a result, an excessive amount of calculation may occur. Thus, to reduce an amount of calculation due to hundreds of millions of finite elements when the FEM is performed for a 3D VOI to be different from a 2D image, a phenomenological local load condition for the VOI should be selected. A detailed operation of selecting the local load condition and localizing the 3D VOI will be described below with reference to FIG. 4.

If the local load condition is selected, the VOI localizing unit 212 may perform the FEM for the VOI based on the local load condition and may calculate a structural behavior value of each of finite elements for a locally provided load.

For example, the VOI localizing unit 212 may perform meshing for the VOI and may represent the VOI as a plurality of finite elements. As the FEM is performed based on bone mineral density (BMD) and a modulus of elasticity of a bone corresponding to a meshed region and a multi-resolution load condition, a structural behavior of each of finite elements may be calculated. For example, the VOI localizing unit 212 may convert BMD into a modulus of elasticity and may obtain a structural behavior value by applying the converted modulus of elasticity and a local load condition to each finite element.

In step 330, the image reconstructing unit 213 may perform topology optimization for high-resolution imaging, may set a multi-resolution constraint for the topology optimization, and may reconstruct a skeletal image in which high-resolution imaging of the VOI is performed.

In this case, the image reconstructing unit 213 may perform topology optimization by setting a separate voxel value in a high-resolution image as a design variable, setting a value of minimizing compliance of the VOI to an objective function, and setting a BMD difference between a high-resolution image and a low-resolution image as a multi-resolution constraint.

For example, the image reconstructing unit 213 may perform topology optimization having a structure where a strain energy of a bone corresponding to the VOI is minimized based on a change amount of the bone, which occurs as a local load condition is applied for each finite element of the VOI.

In this case, to find a structure where compliance is minimized, the image reconstructing unit 213 may extract new BMD (e.g., BMD of a high-resolution image) for the VOI. The image reconstructing unit 213 may convert the new BMD into a modulus of elasticity again and may recalculate a strain energy by applying the converted modulus of elasticity to a finite element. In this case, if a difference value between the new BMD (e.g., the BMD of the high-resolution image) and previous BMD (e.g., BMD of a low-resolution image) used to calculate a strain energy is less than or equal to a reference value, the image reconstructing unit 213 may determine that the topology optimization is completed and may end the topology optimization. In other words, the image reconstructing unit 213 may determine a strain energy calculated based on the previous BMD as a minimum strain energy.

In this case, if the difference value is greater than the reference value, the image reconstructing unit 213 may determine that the minimum strain energy is not found and may repeatedly perform an operation of converting the new BMD into a modulus of elasticity and calculating strain energy by applying the converted modulus of elasticity and a local load condition to a finite element. In this case, finite element modeling and topology optimization may be repeatedly performed until the minimum strain energy is calculated.

Figure 4:
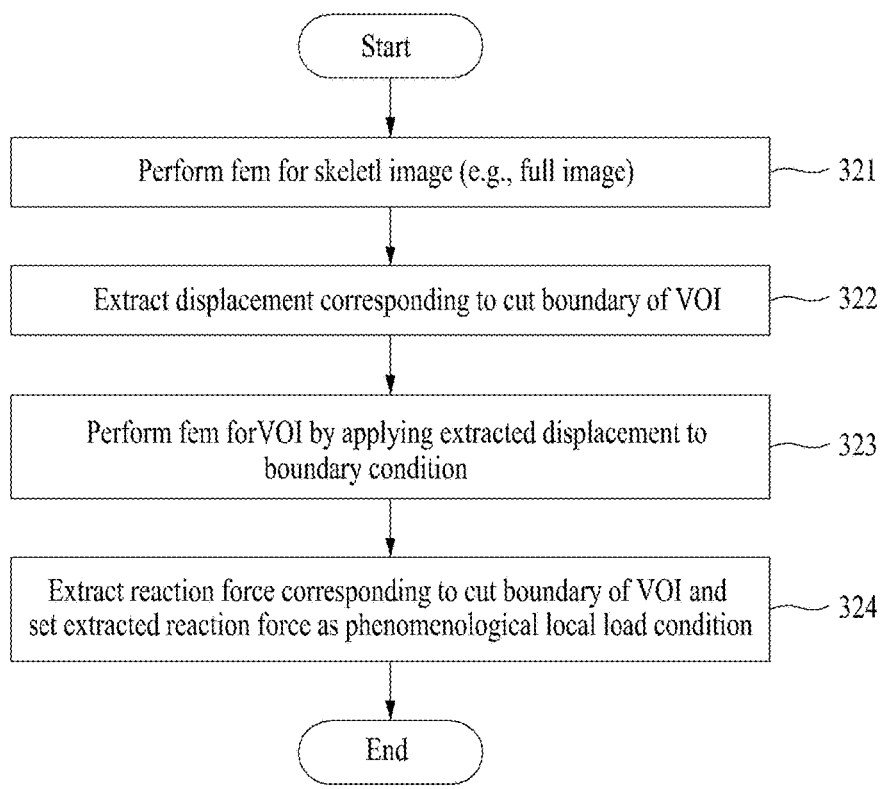
FIG. 4 is a flowchart illustrating an operation of localizing a volume of interest (VOI) in an embodiment of the inventive concept.

FIG. 4 is a flowchart illustrating an operation of localizing a VOI in an embodiment of the inventive concept.

Steps (e.g., steps 321 to 324) of FIG. 4 may be performed by a VOI localizing unit 212 and an image reconstructing unit 213 of FIG. 2.

In step 321, the VOI localizing unit 212 may perform an FEM for a full skeletal image including a VOI.

In step 322, the VOI localizing unit 212 may extract a displacement of a VOI cut boundary from a result calculated by applying a previously defined load condition for each finite element. For example, the load condition may be a daily load case and may include a one-legged stance, abduction, adduction, and the like.

For example, the VOI localizing unit 212 may extract a displacement D of a VOI cut boundary based on Equation 1 below.

$$[K]\{D\}=\{F\} \qquad \text{[Equation 1]}$$

In Equation 1, K may denote a stiffness matrix (i.e., an elastic matrix), D may denote a displacement vector, and F may denote a force vector. In Equation 1, it may be assumed that a displacement boundary condition (BC) is sufficiently suppressed for a rigid body motion of a full model.

Equation 1 above may be represented by being divided into three portions like Equation 2 below.

$$\begin{bmatrix} K_{gg} & K_{gc} & K_{gl} \\ K_{cg} & K_{cc} & K_{cl} \\ K_{lg} & K_{lc} & K_{ll} \end{bmatrix} \begin{Bmatrix} D_g \\ D_c \\ D_l \end{Bmatrix} = \begin{Bmatrix} F_g \\ F_c \\ F_l \end{Bmatrix} \qquad \text{[Equation 2]}$$

In Equation 2, g may denote a global model, l may denote a local mode for a VOI, and c may denote a cut boundary between a full model and the local model. Herein, g may denote a model of representing a region except for the VOI as a finite element in the full model. The full model may be represented as the sum of the global model g, the cut boundary c, and the local model l.

In this case, assuming that there is no force provided to an object to be inspected (i.e., a human body or a specific portion of a human body to be inspected), $\{F_c\}$ and $\{F_l\}$ in Equation 2 may have a value of "0". In other words, a force provided to the VOI and the cut boundary may be "0". In this case, $\{F_g\}$ may be preset. The VOI localizing unit 212 may calculate a displacement $D_c$ corresponding to a VOI cut boundary based on preset $\{F_g\}$ (i.e., a global load), $\{F_c\}$ and $\{F_l\}$ having the value of "0", and Equation 2 above. Herein, the VOI cut boundary may represent a cut boundary between a volume of non-interest corresponding to the other portion except for the VOI and the VOI on a full skeletal image including the VOI.

In step 323, the VOI localizing unit 212 may localize the VOI and may perform a FEM for the localized VOI by applying the calculated displacement $D_c$ of the VOI cut boundary to a BC.

Figure 6:
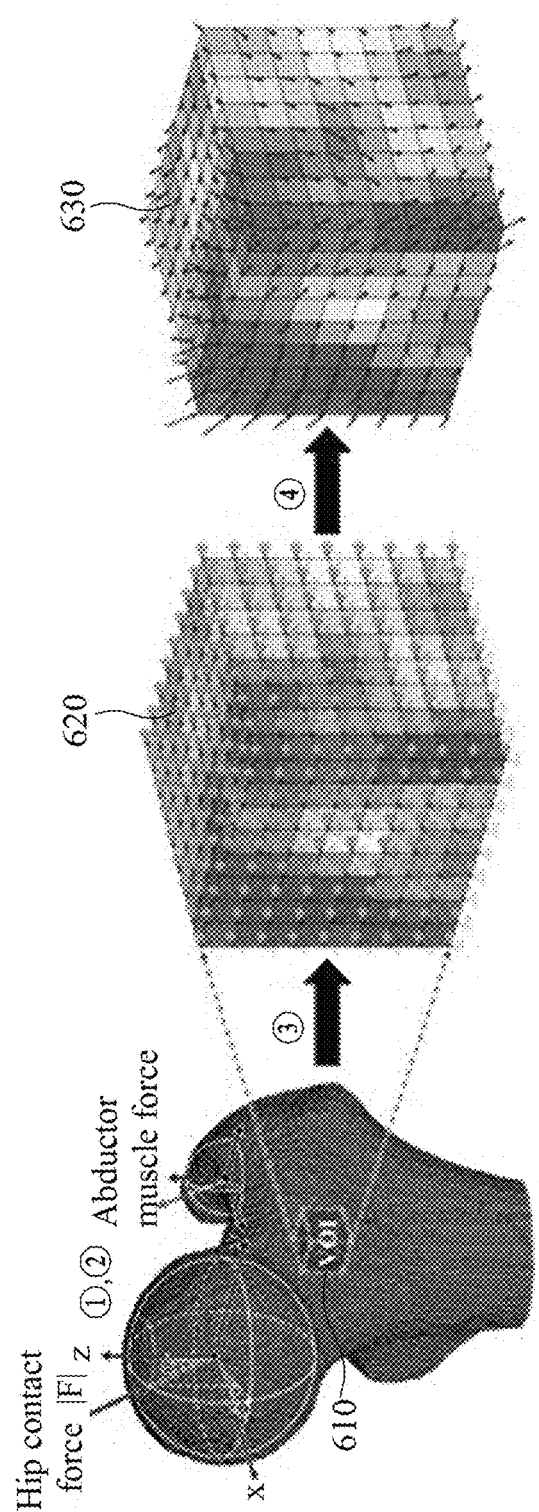
FIG. 6 is a drawing illustrating an operation of localizing a VOI based on displacement on a VOI cut boundary in an embodiment of the inventive concept.

For example, referring to FIG. 6, a VOI 610 may be localized as shown in a reference number 620 of FIG. 6. Equation 2 may be represented again like Equation 3 below.

$$\begin{bmatrix} K'_{cc} & K'_{cl} \\ K'_{ic} & K'_{ll} \end{bmatrix} \begin{Bmatrix} D'_c \\ D'_l \end{Bmatrix} = \begin{Bmatrix} F'_c \\ F'_l \end{Bmatrix} \quad \text{[Equation 3]}$$

Compared with Equation 2, in Equation 3, since an outer surface of a VOI lacks finite elements FEs, a stiffness matrix may have a changed value. In Equation 3, since $\{F'_c\}$ and $\{D'_c\}$ are not known, to solve Equation 3, one of two vectors, for example, $D_c$ obtained in Equation 2 may be replaced with $D'_c$ (i.e., $\{D'_c\} \cong \{D_c\}$). In Equation 3, $\{D'_l\}$ may be represented again like Equation 4 below. $\{F'_c\}$ may be represented again like Equation 5 below.

$$\{D'_l\} = -K_{ll}^{-1}(K'_{lc}\{D'_c\}) \cong -K_{ll}^{-1}(K'_{lc}\{D_c\}) \quad \text{[Equation 4]}$$

$$\{F'_c\} = K'_{cc}\{D'_c\} + K'_{cl}\{D'_l\} \cong K'_{cc}\{D'_c\} + K'_{cl}K_{ll}^{-1}K'_{lc}\{D_c\} \quad \text{[Equation 5]}$$

In Equations 2 and 5 above, a local load condition for the VOI may be estimated based on Equation 6 below.

$$\{\text{Local load for the } VOI\} = \quad \text{[Equation 6]}$$
$$\{F_c\} \cong \{F'_c\} \cong K'_{cc}\{D_c\} - K'_{cl}K_{ll}^{-1}K'_{lc}\{D_c\}$$

In step 323, the VOI localizing unit 212 may perform an FEM for the VOI by applying a displacement to a BC.

For example, as shown in a reference number 630 of FIG. 6, the VOI localizing unit 212 may configure a finite element model corresponding to the VOI to have the local load condition estimated based on Equation 6 above.

In step 324, the VOI localizing unit 212 may extract a reaction force of a VOI cut boundary based on the configured finite element model corresponding to the VOI and may set the extracted reaction force as a phenomenological local load condition.

Figure 5:
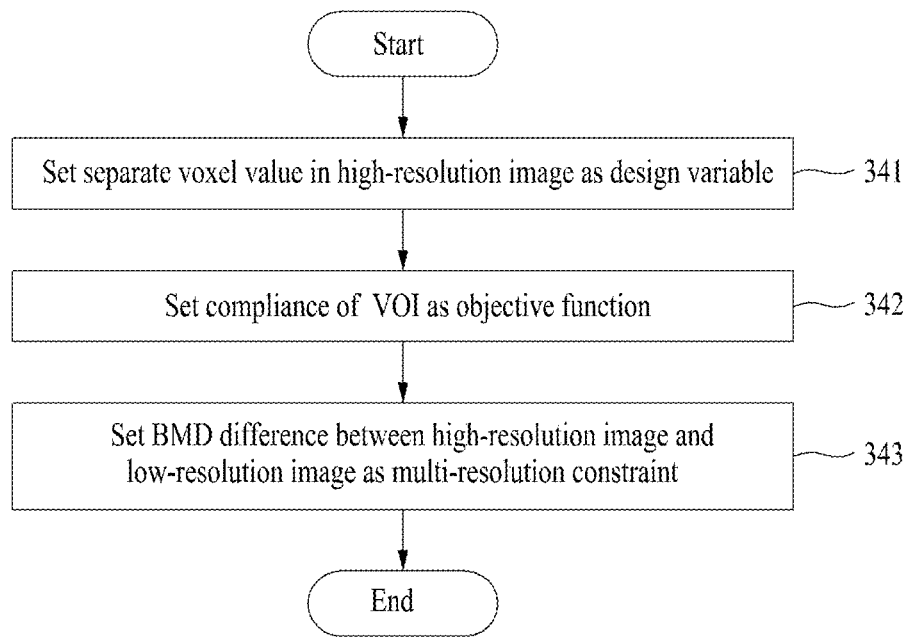
FIG. 5 is a flowchart illustrating an operation of setting a multi-resolution constraint in an embodiment of the inventive concept.

FIG. 5 is a flowchart illustrating an operation of setting a multi-resolution constraint in an embodiment of the inventive concept.

Steps (e.g., steps 341 to 342) of FIG. 5 may be performed by a VOI localizing unit 212 and an image reconstructing unit 213 of FIG. 2.

In step 341, the image reconstructing unit 213 may set a separate voxel value in a high-resolution image as a design variable for topology optimization. Herein, the design variable may indicate BMD. The BMD may be calculated by the separate voxel value in an image corresponding to a VOI represented with a finite element.

In step 342, the image reconstructing unit 213 may set a value for minimizing compliance of the VOI as an objective function. In other words, the objective function may indicate compliance. Topology optimization may be performed until the compliance is minimized.

In step 343, the image reconstructing unit 213 may set a BMD difference between a high-resolution image and a low-resolution image as a multi-resolution constraint.

For example, the image reconstructing unit 213 may set the multi-resolution constraint for the topology optimization based on Equation 7 below.

$$g_x(\rho_{i,j,k}) = \quad \text{[Equation 7]}$$
$$\left(\frac{p}{m}\right)^3 \sum_{i=1}^{\frac{m}{p} \times \frac{m}{p} \times \frac{m}{p}} \left[ \frac{\sum_{j=1}^{p \times p \times p} \sum_{k=1}^{n \times n \times n} \rho_{i,j,k}}{(pn)^3} - \frac{\sum_{j=1}^{p \times p \times p} \rho_{i,j}^{ori}}{p^3} \right]^2 \leq \varepsilon_x^2$$

In Equation 7, $\rho$ may be density which is a design variable and may denote a variable of compliance, and a constraint $g_x(\rho_{i,j,k})$ may denote the BMD difference between the high-resolution image and the low-resolution image. $\varepsilon$ may denote a difference between the high-resolution image and the low-resolution image, and n may denote the number of segmentation per axis to one voxel of the low-resolution image. For example, since there is a small difference between a low-resolution image and a high-resolution image to follow a separate patient BMD distribution of the low-resolution image, E may be previously allocated a very small value. m may denote the number of voxels per axis in the low-resolution image, and $1 \leq p \leq m$ may be met. p may refer to the number of voxels per axis to one voxel of a multi-resolution image. In this case, resolution of the multi-resolution image may establish a relationship which meets the multiplication of resolution of an input original image and p. In other words, p may meet the resolution of the multi-resolution image/the resolution of the original image. For example, referring to FIG. 8, in case of an image of 600 μm resolution, p may correspond to "1". In case of an image of 1200 μm resolution, p may correspond to "2". In case of an image of 1800 μm resolution, p may correspond to "3". In case of an image of 3600 μm resolution, p may correspond to "6".

For example, the constraint may be set to an average value of differences between voxels corresponding to a low-resolution image and an image in which high-resolution imaging is performed (i.e., a high-resolution image).

Figure 7:
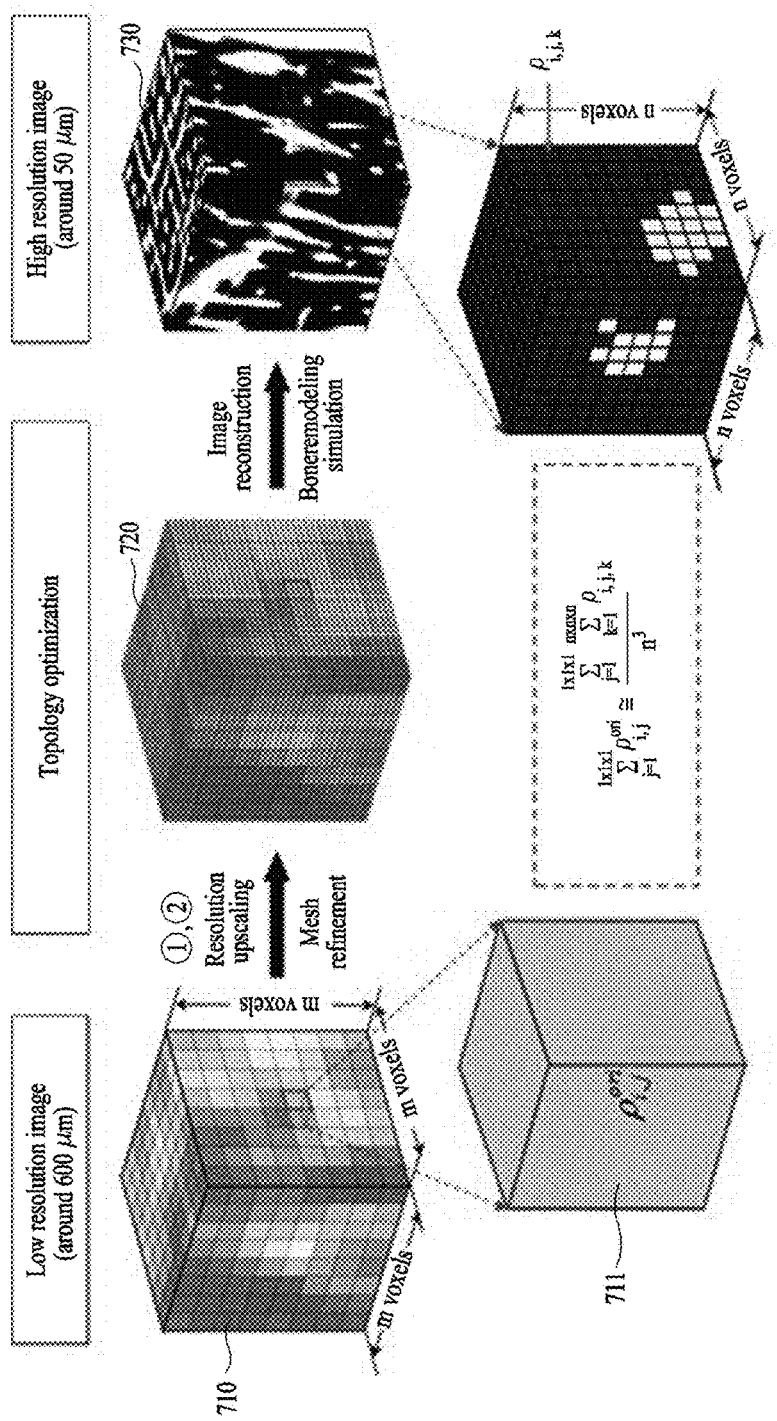
FIG. 7 is a drawing illustrating an operation of performing topology optimization in an embodiment of the inventive concept.

FIG. 7 is a drawing illustrating an operation of performing topology optimization in an embodiment of the inventive concept.

Referring to FIG. 7, a voxel 711 may be subdivided in a 3D low-resolution image (i.e., a 3D BMD medical image 710) corresponding to a VOI. The low-resolution image 710 may be converted into a high-resolution image 720 of the same image through the subdivision of each of voxels. In other words, as the voxel of the low-resolution image corresponding to the VOI is subdivided, the high-resolution image may be generated. A finite element model for the subdivided high-resolution image 720 may be generated. Topology optimization may be performed for the generated finite element model, and the low-resolution image 710 may be reconstructed as the image 730 in which high-resolution imaging is performed, including a bone microstructure.

Figure 8:
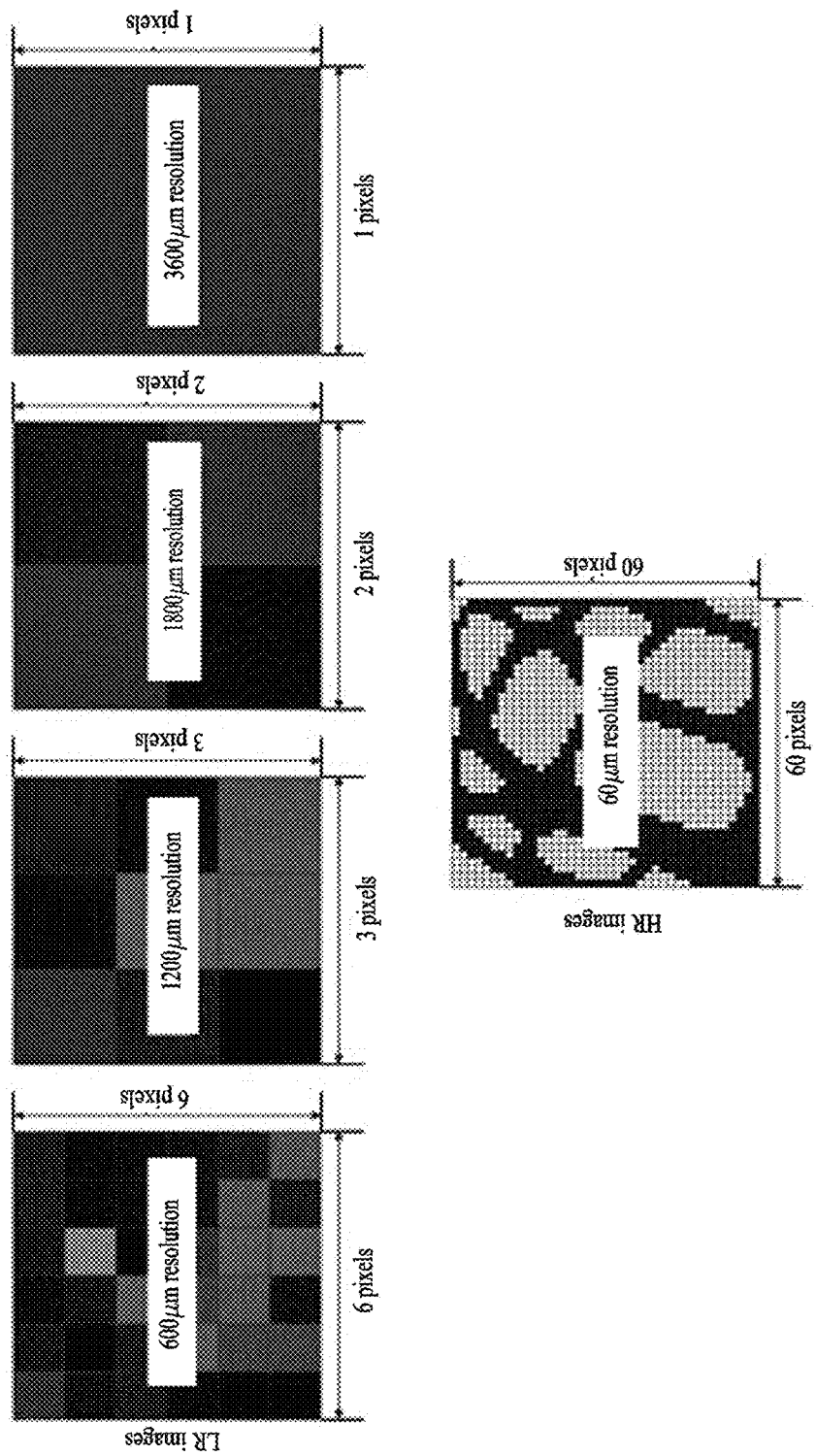
FIG. 8 is a drawing illustrating an operation of setting a multi-resolution constraint by comparing a bone mineral density (BMD) distribution corresponding to a low-resolution image and a high-resolution image with a BMD corresponding to a low-resolution image in an embodiment of the inventive concept.

In this case, as shown in FIG. 8, topology optimization may be performed to improve convergence by comparing a BMD distribution of an image in which high-resolution imaging is performed with a low-resolution image having resolution which is lower than a low-resolution image input from a medical imaging device 101 of FIG. 1 as well as the low-resolution image input from the medical imaging device 101 in a multi-resolution constraint.

If the multi-resolution constraint is set in FIGS. 5 to 7, an image reconstructing unit 213 of FIG. 2 may perform topology optimization by applying the multi-resolution constraint. For example, the image reconstructing unit 213 may perform the topology optimization to which the multi-resolution constraint is applied based on Equation 8 below.

$$\text{Minimize } f(\rho_{i,j,k}) = \sum_{l=1}^{L} c_l \left( \frac{1}{2} u_l^T K u_l \right) \quad \text{[Equation 8]}$$

Subject to $g_1(\rho_{i,j,k}) =$ $$\frac{1}{m^3} \sum_{i=1}^{m \times m \times m} \left( \frac{\sum_{j=1}^{1 \times 1 \times 1} \sum_{k=1}^{n \times n \times n} \rho_{i,j,k}}{n^2} - \sum_{j=1}^{1 \times 1 \times 1} \rho_{i,j}^{ori} \right) \leq \varepsilon_1^2$$

$$g_x(\rho_{i,j,k}) = \left( \frac{p}{m} \right)^3 \sum_{i=1}^{3\frac{m}{p} \times \frac{m}{p} \times \frac{m}{p}} \left( \frac{\sum_{j=1}^{p \times p \times p} \sum_{k=1}^{n \times n \times n} \rho_{i,j,k}}{(pn)^3} - \frac{\sum_{j=1}^{p \times p \times p} \rho_{i,j}^{ori}}{p^3} \right) \leq \varepsilon_x^2$$

$$0.01 \leq \rho_{i,j,k} \leq 1$$

In Equation 8, $f(\rho_{i,j,k})$ may denote an objective function set to compliance, $\rho$ may denote a design variable, and $g_x(\rho_{i,j,k})$ may denote a constraint. When a force $F_i$ is given, $u_l$, may denote a displacement amount of each finite element, and K may denote a stiffness matrix.

By Equation 8, the image reconstructing unit 213 may perform topology optimization of calculating BMD of each of finite elements included in a VOI based on the multi-resolution constraint, until having a value with minimum compliance. A finite element corresponding to density having maximum stiffness for a mechanical force F may be found through this topology optimization, and a high-resolution bone microstructure may be reconstructed based on the found finite element.

Figure 9:
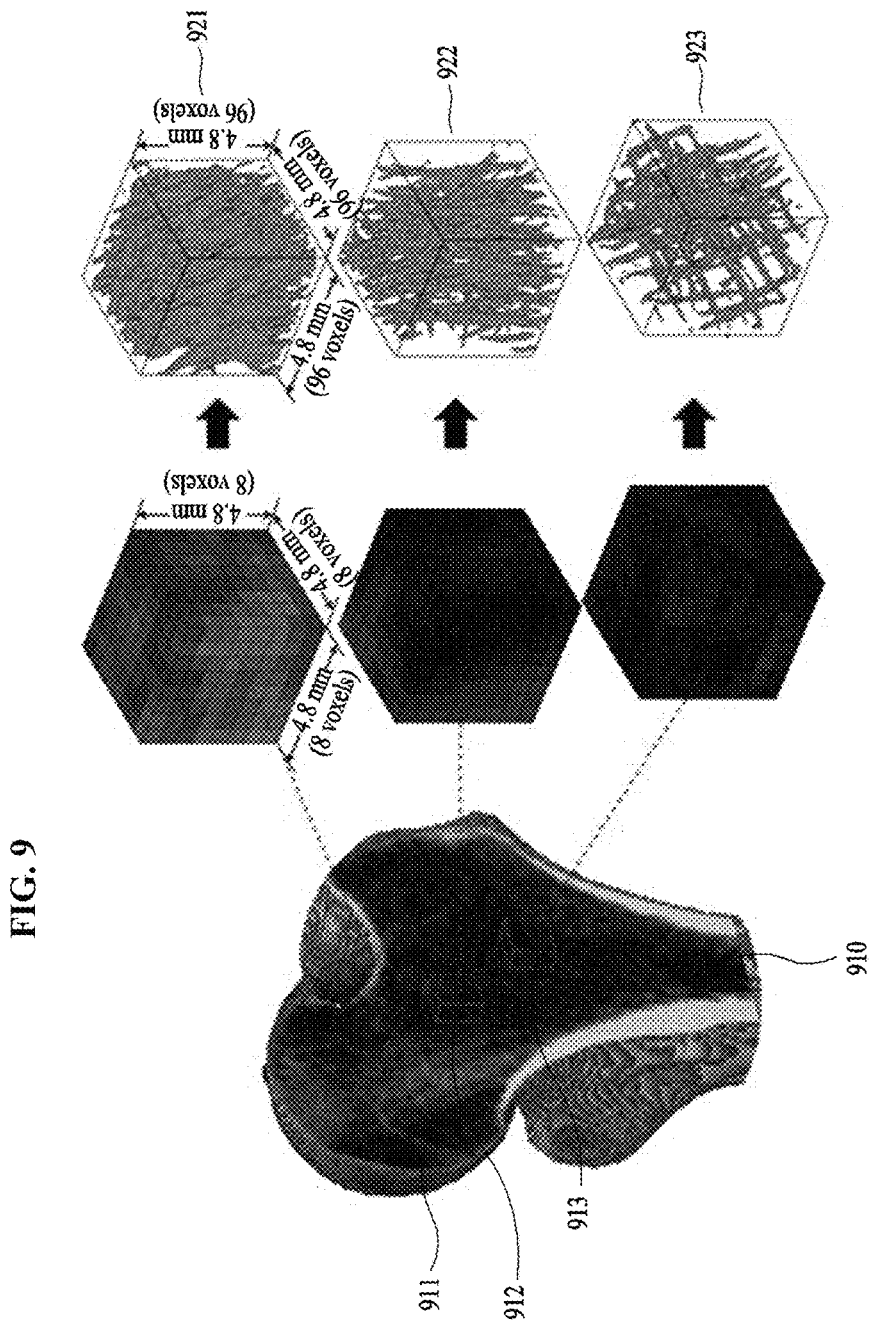
FIG. 9 is a drawing illustrating an operation of reconstructing an image in which high-resolution imaging is performed for a plurality of VOIs in an embodiment of the inventive concept.

FIG. 9 is a drawing illustrating an operation of reconstructing an image in which high-resolution imaging is performed for a plurality of VOIs in an embodiment of the inventive concept.

A description will be given of an operation of performing high-resolution imaging of three VOIs determined for a QCT femur image of a 62-year-old female patient. For example, resolution of the femur image may be about 600 μm.

A region corresponding to a femoral head which is a region to perform high-resolution imaging on a low-resolution 3D femur image 910 may be determined as a first VOI 911. A region corresponding to a femoral neck may be determined as a second VOI 912. A region corresponding to an intertrochanter may be determined as a third VOI 913. For example, each of the first to third VOIs 911 to 913 may be set as a cube shape corresponding to a previously defined size (e.g., 4.8×4.8×4.8 mm³) on the femur image 910.

High-resolution imaging of each of the set first to third VOIs 911 to 913 may be performed with resolution of about 50 μm.

In other words, a local load condition corresponding to each of the first to third VOIs 911 to 913 may be estimated, and a finite element model corresponding to each of the first to third VOIs 911 to 913 may be generated based on the estimated local load condition. In other words, three finite element models may be generated. As topology optimization to which a multi-resolution constraint is applied is performed for each finite element model, high-resolution imaging of each of the first to third VOIs 911 to 913 may be locally performed rather than the entire femur image 910. For example, if a VOI has a size of 10×10×10 mm³ (16×16×16 voxels), the number of finite elements (FEs) of the entire femur image 910 may be 454,567 and the number of FEs corresponding to the VOI may be 4,096. In other words, the requirement number of FEs may decrease to about 97.6% by localizing the VOI. As the topology optimization to which the multi-resolution constraint condition is applied is performed based on Equation 8 above, convergence may be improved by a maximum of 53%.

As such, as shown in FIG. 9, each of the first to third VOIs 911 to 913 is localized and high-resolution imaging is then performed, it may be verified that a distinguishing trabecular bone pattern of each VOI, in which it is impossible to be verified on a low-resolution image, appears on the images 921 to 923 in which the high-resolution imaging is performed. In case of the femoral head image 921, a trabecular bone may be generated in the direction of a principle compressive group. In case of the femoral neck image 922, it may be verified that a trabecular bone of a rod shape is formed due to BMD which is lower that of the femoral neck. In case of the intertrochanter image 923, it may be verified that trabecular bones are orthogonal to each other. As shown in Table 1 below, it may be verified that the images 921 to 923 in which the high-resolution imaging is performed are well reflected to read out characteristics of an actual trabecular bone structure through comparison with a morphometric index.

TABLE 1

| Indices | Femoral head | | Femoral neck | | Intertrochanter | |
|---|---|---|---|---|---|---|
| | Ref. (60-79 years) | Silico. | Ref. (60-79 years) | Silico. | Ref. (60-79 years) | Silico. |
| BV/TV$^a$ | 36.7 ± 8.38 | 36.3 | 18.5 ± 7.21 | 18.4 | 14.2 ± 5.43 | 13.1 |
| Tb. Th$^a$ | 0.22 ± 0.03 | 0.22 | 0.17 ± 0.03 | 0.15 | 0.15 ± 0.02 | 0.13 |
| Tb. Sp$^a$ | 0.40 ± 0.11 | 0.46 | 0.74 ± 0.13 | 0.56 | 0.81 ± 0.19 | 0.62 |
| SMI$^b$ | 1.83 ± 0.58 | 1.37 | 2.18 ± 0.34 | 2.59 | 2.32 ± 0.57 | 2.73 |

As such, a bone microstructure as well as BMD may be verified while an amount of calculation required upon a FEM is reduced by reconstructing an original image as an image in which high-resolution imaging is performed, through the localization for the VOI and the multi-resolution constraint. For example, a bone microstructure for an osteoporosis expression portion may be ascertained, thus increasing reliability of an early diagnosis.

Figure 10:
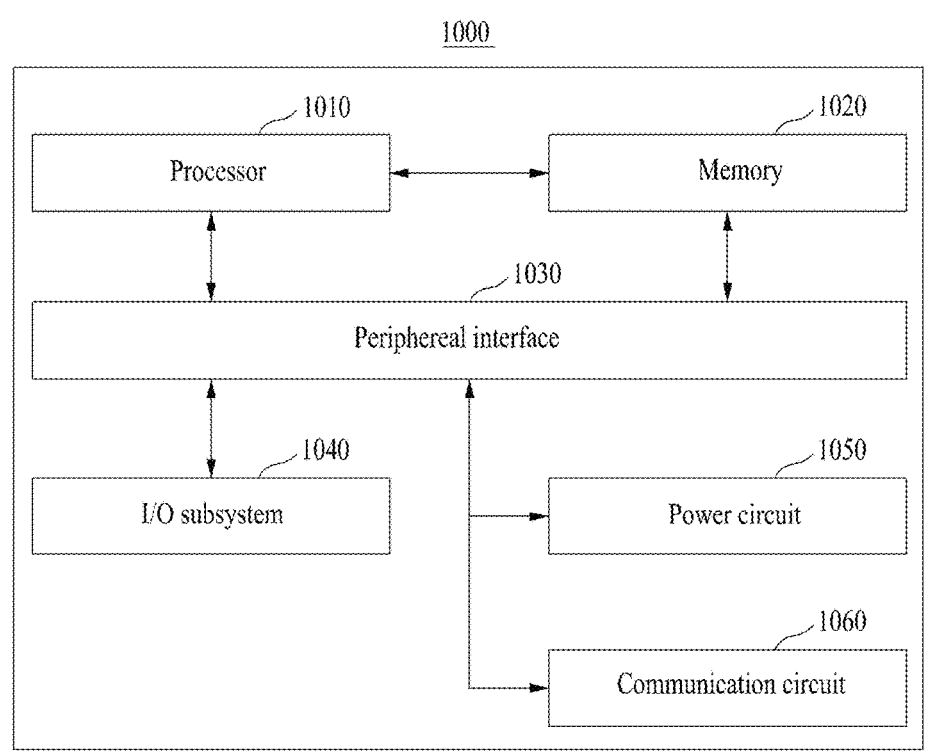
FIG. 10 is a block diagram illustrating a configuration of a computer system in an embodiment of the inventive concept.

FIG. 10 is a block diagram illustrating a configuration of a computer system in an embodiment of the inventive concept. A computer system 1000 may include at least one of at least one processor 1010, a memory 1020, a peripheral interface 1030, an input/output (I/O) subsystem 1040, a power circuit 1050, and a communication circuit 1060. In this case, the computer system 1000 may correspond to a workstation.

The memory 1020 may include, for example, a high-speed random access memory (RAM), a magnetic disc, a static RAM (SRAM), a dynamic RAM (DRAM), a read only memory (ROM), a flash memory, or a non-volatile memory. The memory 1020 may include a software module, a set of instructions, or various other data necessary for an operation of the computer system 1000. In this case, to access the memory 1020 via another component such as the processor 1010 or the I/O interface 1030 may be controlled by the processor 1010.

The peripheral interface 1030 may combine an input and/or output peripheral of the computer system 1000 with the processor 1010 and the memory 1020. The processor 1010 may execute a software module or a set of instructions stored in the memory 1020 to perform various functions for the computer system 1000 and to process data.

The I/O subsystem 1040 may combine various I/O peripherals with the peripheral interface 1030. For example, the I/O subsystem 1040 may include a controller for combining a peripheral, such as a monitor, a keyboard, a mouse, a printer, or a touch screen or sensor if necessary, with the peripheral interface 1030. According to another embodiment, the I/O peripherals may be combined with the peripheral interface 1030 without passing through the I/O subsystem 1040.

The power circuit 1050 may supply to all or some of components of a terminal. For example, the power circuit 1050 may include a power management system, one or more power supplies such as a battery or alternating current (AC), a charging system, a power failure detection circuit, a power converter, an inverter, a power state indicator, or any other components for generating, managing and distributing power.

The communication circuit 1060 may communicate with another computer system using at least one external port. Alternatively, as described above, the communication circuit 1060 may communicate with another computer system by including a radio frequency (RF) circuit if necessary and communicating an RF signal known as an electromagnetic signal.

This embodiment of FIG. 10 is only an example of the computer system 1000. Some components shown in FIG. 10 may be omitted from the computer system 1000. Alternatively, additional components which are not shown in FIG. 10 may be further included in the computer system 1000, or the computer system 1000 may have configuration or arrangement in which two or more components are combined. For example, the computer system 1000 may further include a display and the like other than the components shown in FIG. 10. Components which may be included in the computer system 1000 may be implemented with hardware including an integrated circuit specialized in one or more signaling or applications, software, or combinations thereof.

Methods according to an embodiment may be stored in a computer-readable storage medium by being implemented in the form of program instructions which may be performed via various computer systems.

The foregoing devices may be realized by hardware elements, software elements and/or combinations thereof. For example, the devices and components illustrated in the exemplary embodiments of the inventive concept may be implemented in one or more general-use computers or special-purpose computers, such as a processor, a controller, an arithmetic logic unit (ALU), a digital signal processor, a microcomputer, a field programmable array (FPA), a programmable logic unit (PLU), a microprocessor or any device which may execute instructions and respond. A processing unit may implement an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and may configure a processing unit to operate in a desired manner or may independently or collectively control the processing unit. Software and/or data may be permanently or temporarily embodied in any type of machine, components, physical equipment, virtual equipment, computer storage media or units or transmitted signal waves so as to be interpreted by the processing unit or to provide instructions or data to the processing unit. Software may be dispersed throughout computer systems connected via networks and may be stored or executed in a dispersion manner. Software and data may be recorded in one or more computer-readable storage media.

The methods according to the above-described exemplary embodiments of the inventive concept may be implemented with program instructions which may be executed through various computer means and may be recorded in computer-readable media. The media may also include, alone or in combination with the program instructions, data files, data structures, and the like. The program instructions recorded in the media may be designed and configured specially for the exemplary embodiments of the inventive concept or be known and available to those skilled in computer software. Computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter. The described hardware devices may be configured to act as one or more software modules to perform the operations of the above-described exemplary embodiments of the inventive concept, or vice versa.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

According to an embodiment, the high-resolution imaging apparatus may reconstruct a skeletal image to ascertain a microstructure by performing local high-resolution imaging for a low-resolution skeletal image based on bone remodeling simulations.

According to an embodiment, the high-resolution imaging apparatus may reduce an amount of calculation according to the performance of an FEM for a 3D skeletal image by setting a phenomenological local load condition for a VOI corresponding to part of a skeletal image rather than the entire skeletal image and localizing the VOI.

According to an embodiment, the high-resolution imaging apparatus may improve convergence by setting a multi-resolution constraint and performing topology optimization.

According to an embodiment, the high-resolution imaging apparatus may reduce misdiagnosis according to diagnosing osteoporosis based on only BMD and may more accurately perform an early diagnosis of a lesion such as osteoporosis by linking and providing bone stiffness which may be calculated through a high-resolution image and the FEM with osteoporosis diagnosis criteria, that is, providing an image in which high-resolution imaging is performed to represent BMD and a microstructure.

Further, According to an embodiment, the high-resolution imaging apparatus may reduce an amount of radiation exposure exposed to a human body when an image is captured to diagnose osteoporosis and the like by performing local high-resolution imaging for a VOI in image post-processing rather than image reconstruction, and may provide convenience of an object to be inspected (e.g., a patient) and may increase profitability of a hospital by securing a short capturing time.

Therefore, other implements, other embodiments, and equivalents to claims are within the scope of the following claims.

What is claimed is:

1. A local high-resolution imaging method for a three-dimensional (3D) skeletal image by using a high-resolution imaging device, the method comprising:
   determining a volume of interest (VOI) to perform high-resolution imaging on the 3D skeletal image in which an object to be inspected is captured by using a VOI determining unit of the high-resolution imaging device, wherein the VOI determining unit determines a partial specific portion to perform high-resolution imaging on the 3D skeletal image;
   localizing the VOI based on a finite element method (FEM) by using a VOI localizing unit of the high-resolution imaging device, wherein the VOI localizing unit calculates a structural behavior value of each of finite elements for a locally provided load; and
   setting a multi-resolution constraint based on a bone mineral density (BMD) between the 3D skeletal image and the localized VOI and reconstructing a skeletal image in which high-resolution imaging is performed on the localized VOI by using an image reconstructing unit of the high-resolution imaging device,
   wherein the localizing of the VOI by using the VOI localizing unit comprises:
   performing the FEM for the skeletal image in which the object to be inspected is captured;
   extracting a displacement corresponding to a cut boundary of the VOI based on a previously defined load condition;
   performing the FEM for the VOI by applying the extracted displacement to a boundary condition; and
   extracting a reaction force corresponding to a cut boundary of the VOI in which the FEM is performed and setting the extracted reaction force as a local load condition.

2. The method of claim 1, wherein the determining of the VOI comprises:
   determining a plurality of VOIs on the skeletal image; and
   verifying a trabecular bone corresponding to each of the VOIs based on a skeletal image, in which high-resolution imaging is performed, reconstructed for the plurality of VOIs.

3. A local high-resolution imaging method for a three-dimensional (3D) skeletal image by using a high-resolution imaging device, the method comprising:
   determining a volume of interest (VOI) to perform high-resolution imaging on the 3D skeletal image in which an object to be inspected is captured by using a VOI determining unit of the high-resolution imaging device, wherein the VOI determining unit determines a partial specific portion to perform high-resolution imaging on the 3D skeletal image;
   localizing the VOI based on a finite element method (FEM) by using a VOI localizing unit of the high-resolution imaging device, wherein the VOI localizing unit calculates a structural behavior value of each of finite elements for a locally provided load; and
   setting a multi-resolution constraint based on a bone mineral density (BMD) between the 3D skeletal image and the localized VOI and reconstructing a skeletal image in which high-resolution imaging is performed on the localized VOI by using an image reconstructing unit of the high-resolution imaging device,
   wherein the reconstructing of the skeletal image by using the image reconstructing unit in which the high-resolution imaging is performed comprises:
   setting a separate voxel value in a high-resolution image as a design variable;
   setting compliance of the VOI as an objective function indicating a strain energy of the VOI; and
   setting a BMD difference between the high-resolution image and a low-resolution image as the multi-resolution constraint.

4. The method of claim 3, wherein the high-resolution image is generated by subdividing a voxel of a low-resolution image corresponding to the VOI included in the 3D skeletal image.

5. The method of claim 4, wherein the reconstructing of the skeletal image in which the high-resolution is performed comprises:
   reconstructing a bone microstructure for the VOI by performing topology optimization for a finite element model corresponding to the high-resolution image.

6. A local high-resolution imaging apparatus for a 3D skeletal image, the apparatus comprising:
   a memory into which at least one program is loaded, wherein the memory includes an operating system and a service routine; and
   at least one processor comprising a VOI determining unit, a VOI localizing unit and an image reconstructing unit,
   wherein the VOI determining unit of at least one processor determines a VOI to perform high-resolution imaging on the 3D skeletal image in which an object to be inspected is captured, wherein the VOI localizing unit localizes the VOI based on an FEM, and the image reconstructing unit sets a multi-resolution constraint based on a BMD between the 3D skeletal image and the localized VOI and reconstructs a skeletal image in which high-resolution imaging is performed on the localized VOI, under control of the at least one program, wherein the VOI localizing unit performs the FEM for the skeletal image in which the object to be inspected is captured, extracts a displacement corresponding to a cut boundary of the VOI based on a previously defined load condition, performs the FEM for the VOI by applying the extracted displacement to a boundary condition, and extracts a reaction force corresponding to a cut boundary of the VOI in which the FEM is performed and sets the extracted reaction force as a local load condition.

7. A local high-resolution imaging apparatus for a 3D skeletal image, the apparatus comprising:

a processor, the processor includes a VOI determining unit configured to determine a VOI to perform high-resolution imaging on the 3D skeletal image in which an object to be inspected is captured, wherein the VOI determining unit determines a partial specific portion to perform high-resolution imaging on the 3D skeletal image;

the processor further includes a VOI localizing unit configured to localize the VOI based on an FEM, wherein the VOI localizing unit calculates a structural behavior value of each of finite elements for a locally provided load; and the processor further includes an image reconstructing unit configured to set a multi-resolution constraint based on a BMD between the 3D skeletal image and the localized VOI and to reconstruct a skeletal image in which high-resolution imaging is performed on the localized VOI, wherein the VOI localizing unit performs the FEM for the skeletal image in which the object to be inspected is captured, extracts a displacement corresponding to a cut boundary of the VOI based on a previously defined load condition, performs the FEM for the VOI by applying the extracted displacement to a boundary condition, and extracts a reaction force corresponding to a cut boundary of the VOI in which the FEM is performed and sets the extracted reaction force as a local load condition.

8. The apparatus of claim 7, wherein the VOI determining unit determines a plurality of VOIs on the skeletal image and verifies a trabecular bone corresponding to each of the VOIs based on a skeletal image, in which high-resolution imaging is performed, reconstructed for the plurality of VOIs.

9. A local high-resolution imaging apparatus for a 3D skeletal image, the apparatus comprising:

a processor, the processor includes a VOI determining unit configured to determine a VOI to perform high-resolution imaging on the 3D skeletal image in which an object to be inspected is captured, wherein the VOI determining unit determines a partial specific portion to perform high-resolution imaging on the 3D skeletal image;

the processor further includes a VOI localizing unit configured to localize the VOI based on an FEM, wherein the VOI localizing unit calculates a structural behavior value of each of finite elements for a locally provided load; and the processor further includes an image reconstructing unit configured to set a multi-resolution constraint based on a BMD between the 3D skeletal image and the localized VOI and to reconstruct a skeletal image in which high-resolution imaging is performed on the localized VOI, wherein the image reconstructing unit sets a separate voxel value in a high-resolution image as a design variable, sets compliance of the VOI as an objective function indicating a strain energy of the VOI, and sets a BMD difference between the high-resolution image and a low-resolution image as the multi-resolution constraint.

10. The apparatus of claim 9, wherein the high-resolution image is generated by subdividing a voxel of a low-resolution image corresponding to the VOI included in the 3D skeletal image.

11. The apparatus of claim 10, wherein the image reconstructing unit reconstructs a bone microstructure for the VOI by performing topology optimization for a finite element model corresponding to the high-resolution image.

12. A local high-resolution imaging apparatus for a 3D skeletal image, the apparatus comprising:

a memory into which at least one program is loaded, wherein the memory includes an operating system and a service routine; and at least one processor comprising a VOI determining unit, a VOI localizing unit and an image reconstructing unit, wherein the VOI determining unit of at least one processor determines a VOI to perform high-resolution imaging on the 3D skeletal image in which an object to be inspected is captured, wherein the VOI localizing unit localizes the VOI based on an FEM, and the image reconstructing unit sets a multi-resolution constraint based on a BMD between the 3D skeletal image and the localized VOI and reconstructs a skeletal image in which high-resolution imaging is performed on the localized VOI, under control of the at least one program, wherein the reconstructing of the skeletal image in which the high-resolution imaging is performed comprises:

setting a separate voxel value in a high-resolution image as a design variable;

setting compliance of the VOI as an objective function indicating a strain energy of the VOI; and setting a BMD difference between the high-resolution image and a low-resolution image as the multi-resolution constraint.

13. A non-transitory computer-readable storage medium comprising instructions for controlling a computer system to perform high-resolution imaging of a 3D skeletal image, the instructions controlling the computer system by a method, the method comprising:

determining a VOI to perform the high-resolution imaging on the 3D skeletal image in which an object to be inspected is captured by using a VOI determining unit of a high-resolution imaging device, wherein the VOI determining unit determines a partial specific portion to perform high-resolution imaging on the 3D skeletal image;

localizing the VOI based on an FEM by using a VOI localizing unit of the high-resolution imaging device, wherein the VOI localizing unit calculates a structural behavior value of each of finite elements for a locally provided load; and setting a multi-resolution constraint based on a BMD between the 3D skeletal image and the localized VOI and reconstructing a skeletal image in which high-resolution imaging is performed on the localized VOI by using an image reconstructing unit of the high-resolution imaging device, wherein the localizing of the VOI by using the VOI localizing unit comprises:

performing the FEM for the skeletal image in which the object to be inspected is captured;
extracting a displacement corresponding to a cut boundary of the VOI based on a previously defined load condition;
performing the FEM for the VOI by applying the extracted displacement to a boundary condition; and
extracting a reaction force corresponding to a cut boundary of the VOI in which the FEM is performed and setting the extracted reaction force as a local load condition.

* * * * *